United States Patent [19]

Logan

[11] 4,305,400
[45] Dec. 15, 1981

[54] RESPIRATION MONITORING METHOD AND APPARATUS INCLUDING CARDIO-VASCULAR ARTIFACT DETECTION

[75] Inventor: Charles H. Logan, Portland, Oreg.

[73] Assignee: Squibb Vitatek Inc., Hillsboro, Oreg.

[21] Appl. No.: 84,690

[22] Filed: Oct. 15, 1979

[51] Int. Cl.³ .............................................. A61B 5/05
[52] U.S. Cl. .................................................. 128/670
[58] Field of Search ............... 128/670, 693, 696, 700, 128/708, 716, 723

[56] References Cited

U.S. PATENT DOCUMENTS

| | | | |
|---|---|---|---|
| 3,347,223 | 10/1967 | Pacela | 128/723 |
| 3,524,058 | 8/1970 | Robertson et al. | 128/723 |
| 3,584,618 | 6/1971 | Reinhard et al. | 128/723 |
| 3,677,261 | 7/1972 | Dax | 128/723 |
| 3,976,052 | 8/1976 | Junginger et al. | 128/723 |
| 3,994,284 | 11/1976 | Voelker | 128/693 |

OTHER PUBLICATIONS

Hamilton et al., "Medical Research Engineering", vol. 11, No. 3, May–Jun., 1972, pp. 20–24.

Primary Examiner—William E. Kamm
Attorney, Agent, or Firm—Lawrence S. Levinson

[57] ABSTRACT

A respiration monitor for measuring the variations of the thorax impedance of a patient due to respiration is described. The monitor includes circuitry for suppressing the indication of unwanted signals caused by cardio-vascular activity of the patient. The circuitry receives trigger signals immediately following the QRS complex of the patient's ECG waveform. If a certain negative-going slope is detected in the thorax impedance waveform following the QRS complex, it is counted as a cardio-vascular artifact and not respiration activity. After a predetermined number of cardio-vascular artifact are detected and counted, the respiration monitor is disabled so that this cardio-vascular activity will not reset an apnea counter.

14 Claims, 4 Drawing Figures

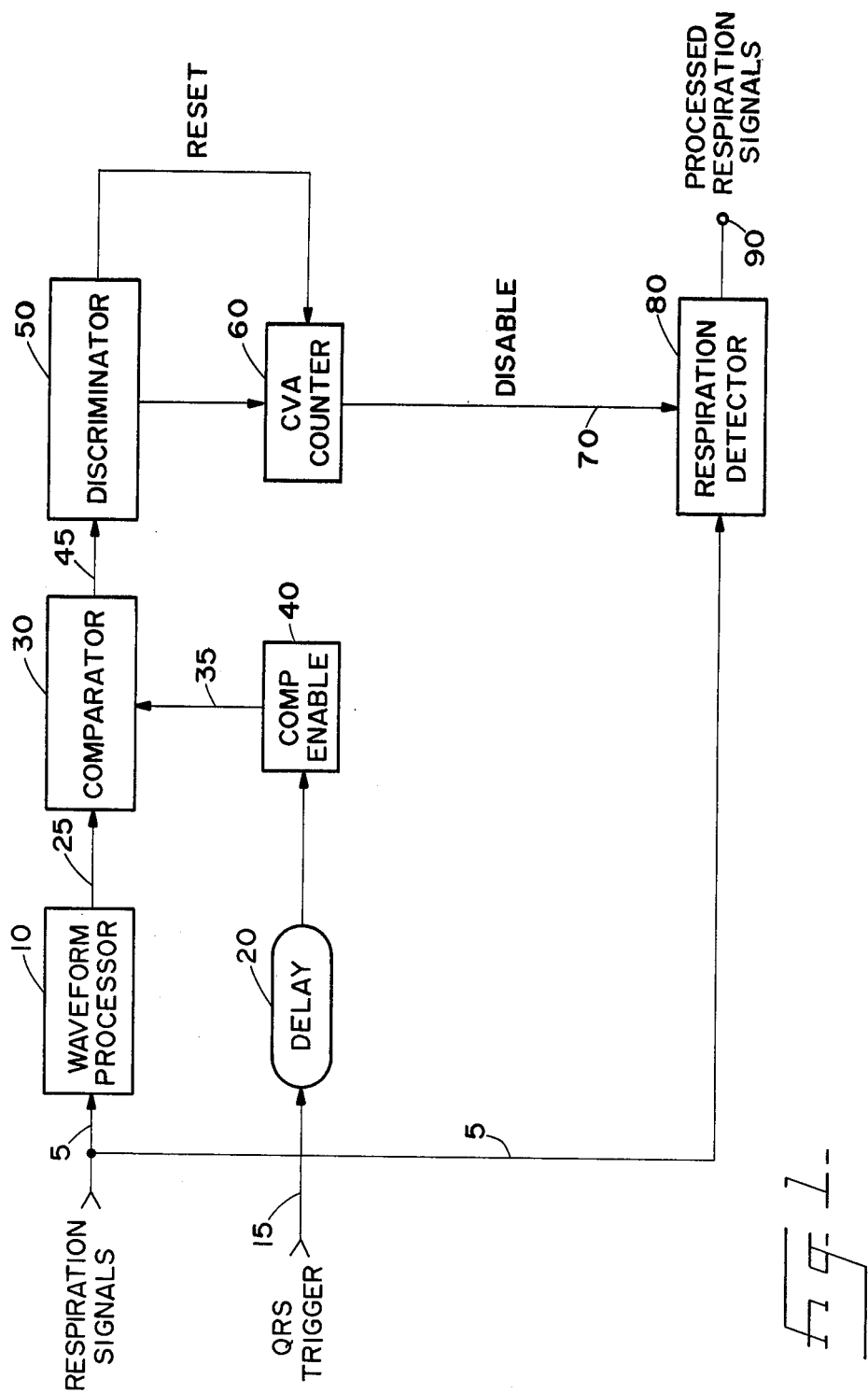

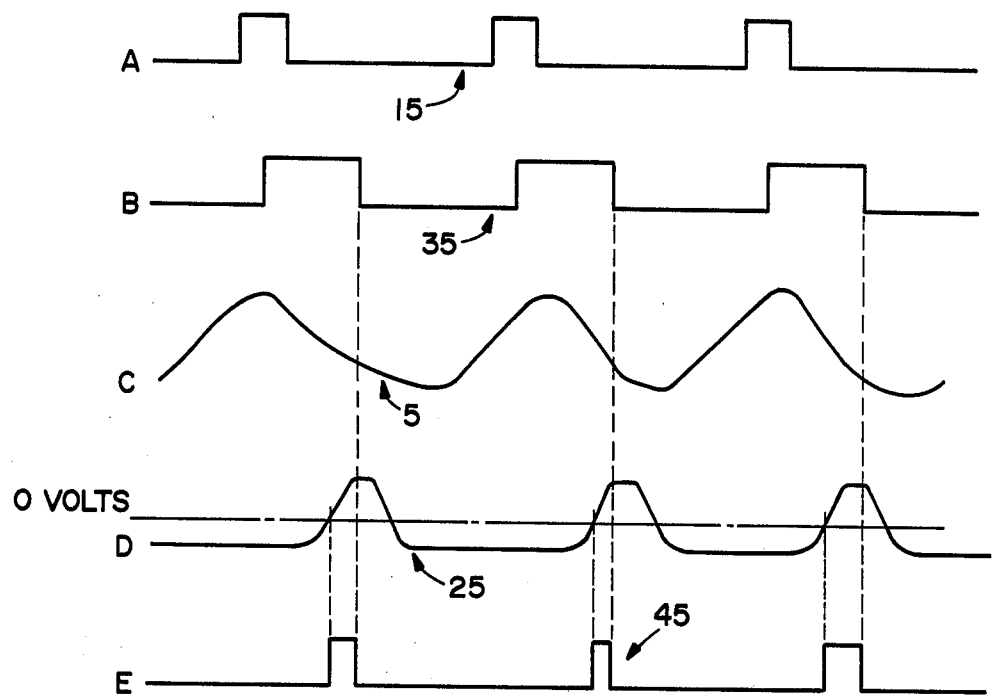
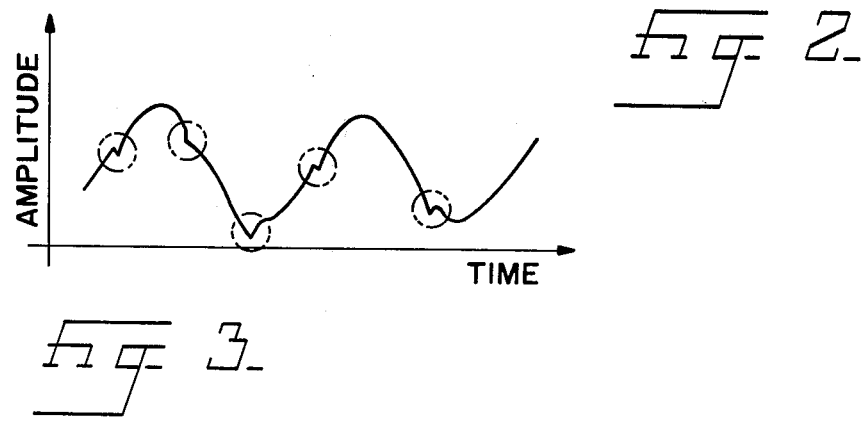
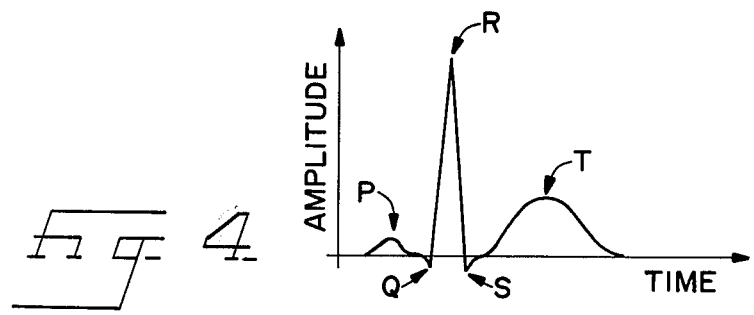

RESPIRATION MONITORING METHOD AND APPARATUS INCLUDING CARDIO-VASCULAR ARTIFACT DETECTION

BACKGROUND OF THE INVENTION

In the field of medical electronics there is a continual need for more reliable measurements of the breathing rate of a human being. The present invention provides means for reliably measuring human respiration. It monitors and processes the change in thoracic impedance to provide breathing rate information. This monitor includes circuitry to prevent the cardiac activity of the patient from being counted as respiratory activity and falsely resetting an apnea timer or the like.

Monitors of this kind monitor the respiration frequency of the patient, record the respiration curve, and indicate respiration irregularities such as apnea. Impedance variations in the thorax region caused by respiration activity are obscured by interferring influences which are primarily introduced by heart activity. This interference is usually referred to as cardio-vascular artifact, hereinafter referred to as CVA. Both respiration activity and heart activity result in a periodic change in the thorax impedance. However, the amplitude of the variation caused by the heart activity is substantially smaller than the variation caused by respiration and the heart beat is usually higher in frequency than the respiration.

In order to suppress disturbances, some known monitors feed the electrical signals obtained by a variation of the thorax impedance to a trigger circuit, which will only deliver an output signal when the amplitude of the supplied input signal exceeds a predetermined threshold value. This threshold value is manually adjustable and is selected so that it is lower than the amplitude of the signals produced by the respiration activity and so that it is higher than the amplitude of the signals caused by the heart activity. One disadvantage of this type of respiration monitor is that the threshold value has to be readjusted frequently as the amplitudes of the respiration signals do not only differ from patient to patient but may also differ with the same patient over an extended period of time. Another difficulty is that the threshold value cannot be adjusted accurately since the periodic impedance variations due to heart activity are generally exceeded by those caused by respiration activity.

In order to avoid such manual readjustment of the trigger threshold, another known type of respiration monitor is provided with a trigger level controller. The controller automatically adjusts the threshold value to a certain fraction, for example to two thirds, of the actual amplitude of the respiration signal. The readjustment occurs with a certain delay so that it will be primarily influenced by respiration signals having a high amplitude, while it tends not to be influenced by interferring signals which occur between those high amplitude signals.

Furthermore, a lower limit is provided for the threshold value, which is higher than the lowest amplitudes of the respiration signals. This lower limit, however, should be higher than the highest possible amplitude of the heart beat signals. In practice, these two requirements cannot be met simultaneously, as the amplitude of the respiration signals may be equal or smaller than that of the signals introduced by the heart activity. If the lower limit of the threshold value is made so high that it is above the amplitude of the heart signals in all cases, it may happen that the respiration monitor does not respond to weak respiration signals. If the lower limit for the threshold value is low enough for weak respiration signals, the automatic readjustment may fail if apnea occurs or if the amplitude of the respiration signals is not substantially higher than that of the heart signals. In these cases, there will result a threshold value which has a lower amplitude than the heart signals. Consequently, the trigger circuit will supply output signals which are caused by heart activity and which will, thus, result in wrong indication of the respiration activity.

SUMMARY OF THE INVENTION

According to the present invention respiration signals obtained from an impedance pneumograph are applied to a waveform processor which accentuates those portions of the respiration signals having a certain rapid decrease in impedance. In respiration signals of this kind, the cardio-vascular activity usually produces a repeating rapid decrease in impedance.

The respiration signals are first differentiated and filtered to accentuate slopes having a certain negative rate of change of impedance, hereinafter referred to a $-dz/dt$. CVA appears as a negative-going slope in the respiration signals immediately following the QRS complex of the patient's ECG signal. Consequently, an enabling signal is generated after the detection of each QRS complex. This signal enables a comparator and if a respiration signal takes a downward turn during the duration of the enabling signal, the comparator generates a pulse. This pulse is counted by a counter which is reset if an enabling signal occurs without the coincidence of a CVA. When a CVA has been detected four consecutive times, the monitor's respiration detection circuitry is disabled. This prevents the CVA from being counted as respiration and, furthermore, prevents erroneous resetting of an apnea timer.

It is therefore an object of the present invention to provide a reliable impedance pneumograph.

It is another object of the present invention to provide a means to accurately detect CVA in respiration signals.

It is a further object to provide reliable method and apparatus for analysis of respiration signals on a heart beat-to-heart beat basis.

It is yet another object of the present invention to provide a CVA detection circuit that will not erroneously reset an apnea timer.

BRIEF DESCRIPTION OF THE DRAWINGS

Various features and advantages of the present invention will become more apparent upon consideration of the following description taken in conjunction with the accompanying drawings, wherein:

FIG. 1 is a block diagram of a respiration monitor according to the present invention;

FIG. 2 is a waveform ladder diagram showing the time relationship of various waveforms throughout the system of FIG. 1;

FIG. 3 is a typical respiration signal obtained via an impedance pneumograph; and FIG. 4 is a typical ECG signal showing the QRS complex.

DETAILED DESCRIPTION OF THE PREFERRED EMBODIMENT

Turning now to the drawings, FIG. 1 shows a block diagram of the respiration monitor according to a preferred embodiment of the present invention. Each block of the block diagram comprises circuitry well known in the art. An exhaustive description of circuit operation is, therefore, not felt to be necessary. Instead, each block will be discussed in accordance with its contribution to the overall system. Those desiring detailed information concerning respiration monitoring are referred to *Biophysical Measurements,* copyright 1970, Tektronix, Inc.

One input to a monitor according to the present invention is respiration signals 5 such as those shown in FIG. 3. The respiration signals may be obtained from an impedance pneumograph (not shown). This apparatus is normally comprised of a pair of electrodes attached to the skin of the patient near the thoracic cavity region. These electrodes conduct electric current through the cavity in response to a source of electric power connected in series. The power source is usually a constant source of alternating current.

The thorax presents an electrical impedance to the electrodes which consists of two impedance components: a relatively steady value of impedance known as mean thoracic impedance and a varying value of impedance known as respirative impedance. The respirative impedance varies with inhaling and exhaling and thus is a measure for the respiration activity of the patient. The pneumograph may also contain an impedance meter preferably comprising an impedance measuring bridge as well as a demodulator and an amplifier. The output of the impedance meter is respiration wave 5, similar to that shown in FIG. 3. Such impedance pneumographs are well known to those skilled in the art.

A second input to a respiration monitor according to the present invention is a pulse 15, such as that shown in FIG. 2A generated from the heart beat. This pulse may be taken from a conventional ECG monitor (not shown) connected to the patient and is preferably a pulse which occurs after the completion of the well-known QRS complex. The duration of pulse 15 may typically be 100 milliseconds. A typical ECG waveform including the QRS complex is shown in FIG. 4.

Referring to FIG. 3, the negative deflections riding on respiration signals 5 are representative of CVA activity. FIG. 2C is an expanded respiration signal 5 showing the CVA activity in detail. The CVA activity has the characteristic of exhibiting a negative change in impedance following the QRS complex. The negative-going slope or decrease in thoracic impedance of CVA activity is caused by perfusion of blood through the pulmonary vascular system, initiated by the left ventricular ejection action of the heart.

Respiration signal 5 is first coupled to a waveform processor 10. Processor 10 may be a differentiator, rectifier, limiter, and filter network which accentuates the portions of respiration signal 5 that have a certain negative dz/dt and attenuates the remainder of the signal. CVA's typically have a dz/dt of −4 or −5 Ω/second. The differentiated output signal 25 is shown in FIG. 3D. Signal 25 is then coupled to comparator 30, another input to which is an enabling signal 35, shown in FIG. 2B. Enabling signal 35 is generated from the aforementioned QRS trigger pulse 15.

Enabling pulse 35 is generated in the following manner. QRS trigger pulse 15 is first coupled to delay device 20 which may have a delay of 50 milliseconds. This delay compensates for the electro-mechanical lag inherent in heart muscle dynamics that occurs after the QRS complex is generated and before the decrease in impedance caused by left ventricular ejection appears in the respiration signal. The delayed QRS trigger pulse is then coupled to comparator enable 40 which may be a timer that generates an output pulse for 215 milliseconds. This output pulse is the enabling pulse 35 referred to above and shown in FIG. 2B.

Thus, enabling pulse 35 enables comparator 30 for a time period equal to, for example, 215 milliseconds. Comparator 30 may be a commercially available comparator referenced to a predetermined level such as ground. Therefore, comparator 30 will detect the zero crossings of differentiated respiration signal 25. The output of comparator 30 is pulse 45 with a rising edge falling within time period 35 such as that shown in FIG. 3E. However, the rising edge of pulse 45 will only be significant if a zero crossing occurs in signal 25 during the aforementioned 215-millisecond time period.

Pulse 45 is routed to discriminator 50 which may be any conventional time discriminator which will act only on rising pulse edges that fall within a predetermined recognition interval. Each rising edge that falls within the recognition interval will produce a qualified output pulse from discriminator 50. The output of discriminator 50 is a pulse which is applied to the count input of a CVA counter 60. If, however, there is no qualified pulse present at the input of discriminator 50, it will generate a reset pulse which is routed to the reset input of counter 60.

Counter 60 receives and counts the output pulses from discriminator 50 until a predetermined number of consecutive pulses are received. Counter 60 then generates a disable signal 70 after it counts, for example, four consecutive pulses. Any number of pulses may be used to ensure that a CVA activity is present.

Respiration detector 80 receives respiration signals 5 from the aforementioned impedance pneumograph and gates them to output terminal 90 if disable signal 70 is not present. This is the normal mode of operation when there is no CVA activity present. If, however, a disable signal 70 is present at the input of respiration detector 80, respiration signals 5 will not be gated to the output. Therefore, the CVA activity will not be treated as respiration signals and will not produce erroneous respiration information or falsely reset an apnea counter.

It will be obvious to those skilled in the art that many changes may be made in the details of the above-described preferred embodiment of the present invention without departing from the broader aspects thereof. Therefore, the appended claims are intended to cover all such changes that fall within the scope of the invention.

I claim as my invention:

1. Apparatus for monitoring the respiration and heartbeat activity of a patient and for producing an indication whenever respiration is absent for a predetermined number of successive heartbeats, said apparatus being for use with a first and second input signal producing means for producing a first and second input signal respectively said first input signal having a first component indicative of patient respiration and a second component indicative of patient heartbeat; said first signal having a slope;

said second input signal indicative of patient heartbeat alone said apparatus comprising:

(a) processor means responsive to said first signal and said slope of said first signal for producing a third signal whenever the slope of said first signal exceeds a predetermined value;

(b) comparator enable means for producing an enable pulse, said comparator enable means being responsive to said second input signal;

(c) comparison means associated with said processor means for producing an output signal whenever said third signal begins within a predetermined period of time, determined by said comparator enable means, after the receipt of said enable pulse by said comparison means and for producing a reset signal whenever said third signal does not begin within said predetermined period of time; and (d) counter means for producing a disable signal whenever a predetermined number of output signals are produced without the intermediate production of a reset signal, said disable signal being indicative of an absence of respiration for a predetermined number of successive heartbeats.

2. The apparatus of claim 1 wherein said predetermined slope value is negative.

3. The apparatus of claim 2 wherein said first input signal producing means is responsive to respirative impedance and CVA activity and said first input signal is a time-varying function of respirative impedance and CVA activity, and wherein said slope value is within the range of from $-4$ to $-5$ $\Omega$/sec.

4. The apparatus of claim 1 wherein said first input signal producing means is responsive to respirative impedance and CVA activity, and said heartbeat component of said first input signal is representative of a decrease in thoractic impedance caused by said heartbeat and said second input signal producing means provides said second input signal as digital pulse representative of the completion of each QRS complex of a patient ECG waveform, and wherein said second receiving means includes delay means for delaying said second input signal, whereby said second input signal is delayed a time to compensate for the electromechanical lag inherent in heart muscle dynamics between the generation of the QRS complex and a respective decrease in thoractic impedance.

5. The apparatus of claim 4 wherein said delay time is approximately 50 milliseconds.

6. The apparatus of claim 1 wherein said predetermined number of output signals is four.

7. The apparatus of claim 1 further comprising an output terminal and a respiration detector comprising gating means, said respiration detector for receiving said first input signal and for gating said signal to said output terminal only when said disable signal is absent.

8. The apparatus of claim 1 wherein said predetermined period of time is within the range from 50 to 265 millisecond.

9. A method of monitoring the respiration and heartbeat activity of a patient and of providing an indication whenever respiration is absent for a predetermined number of successive heartbeats, said method comprising the steps of:

(a) providing a first input signal having a slope and a first component indicative of patient respiration and a second component indicative of patient heartbeat;

(b) providing a second input signal indicative of patient heartbeat alone;

(c) providing a comparator means;

(d) producing a third signal whenever the slope of said first input signal exceeds a predetermined value;

(e) enabling said comparator means for a period of time after the receipt by said comparator means of said second signal;

(f) producing an output signal whenever said third signal begins within a predetermined period of time after the receipt by said comparator means of said second signal, and producing a reset signal whenever said third signal does not begin within said predetermined period of time, (g) producing a disable signal whenever a predetermined number of output signals are produced without the intermediate production of a reset signal, said disable signal being indicative of an absence of respiration for a predetermined number of successive heartbeats.

10. The method of claim 9 wherein said predetermined slope value is negative said predetermined slope value being for comparison with the slope of said first input signal.

11. The method of claim 10 wherein said first input signal is a time-varying function of respirative impedance and CVA activity, and wherein said slope value is within the range from $-4$ to $-5$ $\Omega$/sec.

12. The method of claim 9 further comprising providing gating means and an output terminal and the step of controlling the passage of said first input signal to said output terminal by said gating means, said gating means only passing said first input signal when said disable signal is absent.

13. The method of claim 9 wherein said predetermined period of time is within the range from 50 to 265 millisecond.

14. The method of claim 9 wherein said heartbeat component of said first input signal is representative of a decrease in thoractic impedance caused by said heartbeat and said second signal is a digital pulse representative of the completion of each QRS comples of a patient ECG waveform, and wherein said step (f) includes delaying said second input signal, whereby the electromechanical lag inherent in heart muscle dynamics between the generation of the QRS complex and a respective decrease in thoractic impedance is compensated for.

* * * * *

UNITED STATES PATENT AND TRADEMARK OFFICE
CERTIFICATE OF CORRECTION

PATENT NO. : 4,305,400
DATED : December 15, 1981
INVENTOR(S) : Charles H. Logan

It is certified that error appears in the above-identified patent and that said Letters Patent are hereby corrected as shown below:

In Claim 4, line 40, column 5, change "compnent" to
-- component --.

In Claim 14, line 55, column 6, change "comples" to -- complex --

Signed and Sealed this

Ninth Day of March 1982

[SEAL]

Attest:

Attesting Officer

GERALD J. MOSSINGHOFF

Commissioner of Patents and Trademarks